United States Patent
Ohishi et al.

(10) Patent No.: US 11,519,985 B2
(45) Date of Patent: Dec. 6, 2022

(54) MRI APPARATUS AND ITS COMMUNICATION METHOD

(71) Applicant: CANON MEDICAL SYSTEMS CORPORATION, Otawara (JP)

(72) Inventors: Takafumi Ohishi, Yokohama (JP); Sadanori Tomiha, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 366 days.

(21) Appl. No.: 16/813,850

(22) Filed: Mar. 10, 2020

(65) Prior Publication Data

US 2020/0292650 A1   Sep. 17, 2020

(30) Foreign Application Priority Data

Mar. 12, 2019  (JP) .............................. JP2019-044665

(51) Int. Cl.
*G01R 33/36*  (2006.01)
*G01R 33/565*  (2006.01)
(Continued)

(52) U.S. Cl.
CPC .......... *G01R 33/3692* (2013.01); *A61B 5/055* (2013.01); *A61B 5/721* (2013.01); *G01R 33/56509* (2013.01); *G01R 33/56545* (2013.01)

(58) Field of Classification Search
CPC .......... G01R 33/3692; G01R 33/56509; G01R 33/56545; G01R 33/5673; G01R 33/36;
(Continued)

(56) References Cited

U.S. PATENT DOCUMENTS 5,473,252 A * 12/1995 Renz .................. G01R 33/3642
                                                              324/318
2010/0117649 A1  5/2010 Nakanishi et al.
(Continued)

FOREIGN PATENT DOCUMENTS

CN    102103195 A    6/2011
CN    106774634 A    5/2017

OTHER PUBLICATIONS

Extended European Search Report dated Aug. 7, 2020 in European Patent Application No. 20162160.4, 12 pages.
(Continued)

*Primary Examiner* — Rishi R Patel
(74) *Attorney, Agent, or Firm* — Oblon, McClelland, Maier & Neustadt, L.L.P.

(57) ABSTRACT

In one embodiment, a Magnetic Resonance Imaging (MRI) apparatus includes: an RF coil configured to perform A/D conversion on a magnetic resonance (MR) signal received from an object and wirelessly transmit the MR signal; a main body configured to wirelessly receive the MR signal and generate a system clock; first communication circuitry configured to transmit the system clock by surface electric field communication using electric field propagation along a body surface of the object; and second communication circuitry provided in the RF coil and configured to receive the system clock transmitted by the surface electric field communication, wherein the RF coil is configured to operate based on the received system clock.

14 Claims, 11 Drawing Sheets

(51) Int. Cl.
*A61B 5/00* (2006.01)
*A61B 5/055* (2006.01)

(58) Field of Classification Search
CPC ..... A61B 5/055; A61B 5/1102; A61B 5/1135; A61B 5/002; A61B 5/024; A61B 5/0004; A61B 5/0015; A61B 5/08; H04B 13/005
See application file for complete search history.

(56) References Cited

U.S. PATENT DOCUMENTS

| | | |
|---|---|---|
| 2012/0161773 A1 | 6/2012 | Evers et al. |
| 2014/0021956 A1 | 1/2014 | Tomiha et al. |
| 2016/0245888 A1* | 8/2016 | Bollenbeck ...... G01R 33/56308 |
| 2017/0176552 A1 | 6/2017 | Reykowski |
| 2020/0166597 A1* | 5/2020 | Speier ................. H04B 13/005 |

OTHER PUBLICATIONS

J. Ryckaert, et al., "Channel model for wireless communication around human body," Electronic Letters, vol. 40, No. 9, XP006021831, Apr. 29, 2004, 2 pages.
Gareth A. Conway, et al., "Antennas for Over-Body-Surface Communication at 2.45 GHz," IEEE Transactions on Antennas and Propagation, vol. 57, No. 4, XP011255091, Apr. 2009, pp. 844-855.
Combined Chinese Office Action and Search Report dated Apr. 1, 2022, in corresponding Chinese Patent Application No. 202010168879.6 (with English Translation and English Translation of Category of Cited Documents), 9 pages.

* cited by examiner

MRI APPARATUS AND ITS COMMUNICATION METHOD

CROSS-REFERENCE TO RELATED APPLICATION

This application is based upon and claims the benefit of priority from Japanese Patent Applications No. 2019-044665, filed on Mar. 12, 2019, the entire contents of which are incorporated herein by reference.

TECHNICAL FIELD

Disclosed Embodiments relate to a magnetic resonance imaging (MRI) apparatus and its communication method.

BACKGROUND

An MRI apparatus is an imaging apparatus that magnetically excites nuclear spin of an object placed in a static magnetic field by applying a radio frequency (RF) pulse having the Larmor frequency and reconstructs an image on the basis of magnetic resonance (MR) signals emitted from the object due to the excitation.

In the MRI apparatus, the RF pulse is transmitted from a whole-body (WB) coil toward the object. The MR signal emitted from the object in response to the transmission is received by the WB coil or an RF coil. The RF coil receives the MR signal emitted from the object at a position close to the object. Depending on the anatomical imaging part of the object, there are various RF coils such as for the head, for the chest, for the spine, and for the lower limbs. The RF coil is also referred to as a local coil or a surface coil.

Conventionally, a wired RF coil has been widely used. The wired RF coil is configured to transmit an MR signal, which is received from the object, to the main body of the MRI apparatus by wire. On the other hand, a wireless RF coil has also been developed, which converts the received MR signal from an analog signal to a digital signal by using an A/D converter and wirelessly transmits the digitized MR signal to the main body of the MRI apparatus. The "main body of the MRI apparatus" may be hereinafter simply referred to as the "main body".

When using the wired RF coil, the main body performs A/D conversion on the MR signal transmitted as an analog signal from the wired RF coil to the main body by using an AD clock generated from the system clock in the main body. On the other hand, when using the wireless RF coil, an AD clock for performing A/D conversion on the MR signal is required on the RF coil side, and a system clock for generating the AD clock is also required on the RF coil side.

The digitized MR signal is transmitted to the main body, and various types of digital processing is performed on the digitized MR signal by using a system clock which is generated in the main body. Thus, it is required that the system clock used on the RF coil side and the system clock generated in the main body are synchronized with each other.

In order to synchronize both system clocks, it may be conceivable to wirelessly transmit the system clock in the main body to the RF coil. However, in a conventional remote wireless communication system, there may occur a situation in which stable transmission of the system clock becomes difficult due to the effects of fading occurring in the wireless propagation path.

Apart from the situation about the transmission of the system clock described above, there is a strong demand to readily obtain biological information such as heartbeat and respiration of the object without imposing a burden on the object.

DETAILED DESCRIPTION

In one embodiment, a Magnetic Resonance Imaging (MRI) apparatus includes: an RF coil configured to perform A/D conversion on a magnetic resonance (MR) signal received from an object and wirelessly transmit the MR signal; a main body configured to wirelessly receive the MR signal and generate a system clock; first communication circuitry configured to transmit the system clock by surface electric field communication using electric field propagation along a body surface of the object; and second communication circuitry provided in the RF coil and configured to receive the system clock transmitted by the surface electric field communication, wherein the RF coil is configured to operate based on the received system clock.

First Embodiment

Hereinbelow, the first embodiment of the present invention will be described by referring to the accompanying drawings.

Figure 1:
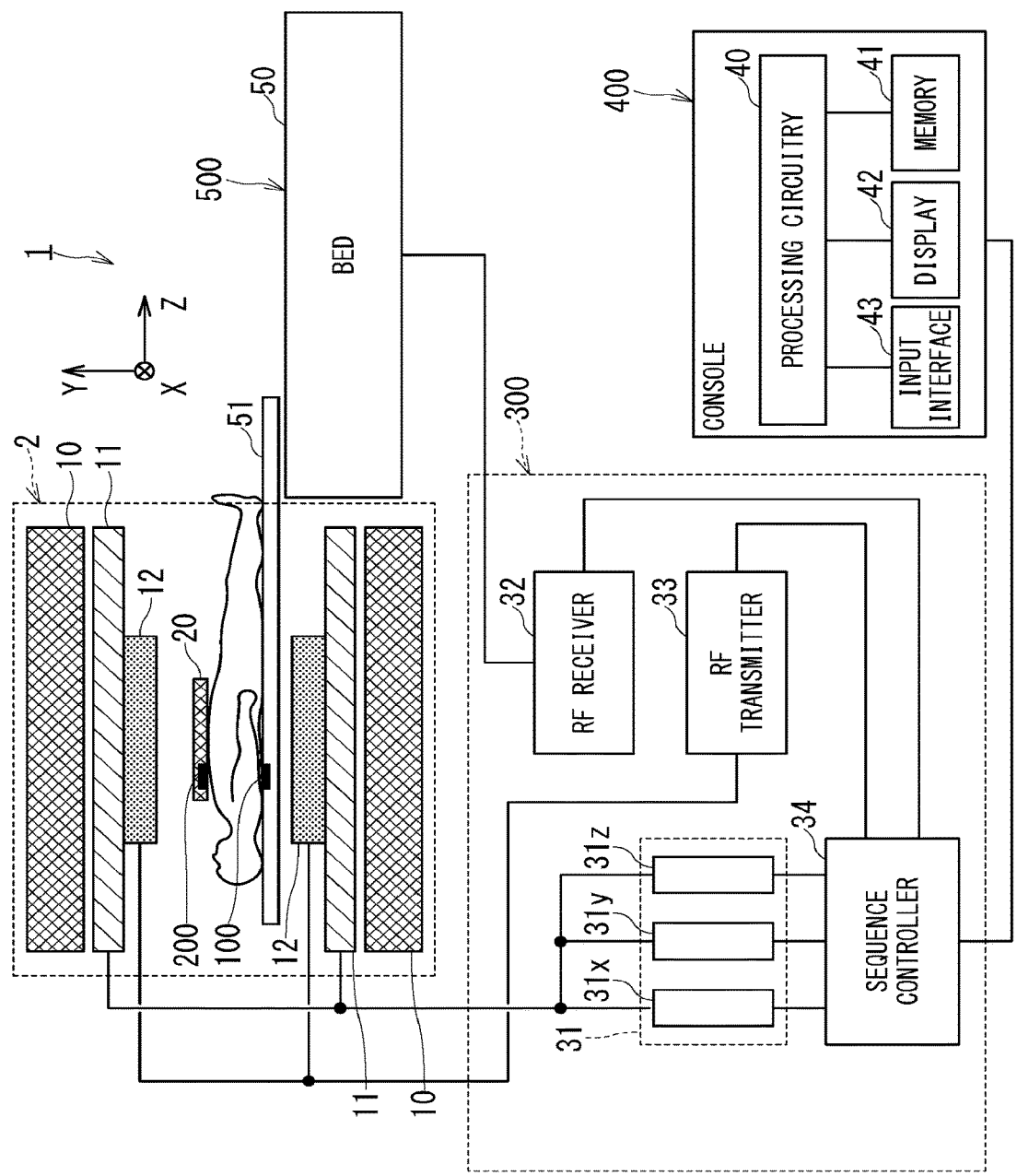
FIG. 1 is a configuration diagram illustrating an overall configuration of an MRI apparatus according to each embodiment.

FIG. 1 is a block diagram illustrating an overall configuration of an MRI apparatus 1 according to the first embodiment. The MRI apparatus 1 of the first embodiment includes a gantry 2, a control cabinet 300, a console 400, and a bed 500.

The gantry 2 includes a static magnetic field magnet 10, a gradient coil assembly 11, and a whole body (WB) coil 12, and these components are housed in a cylindrical housing. The bed 500 includes a bed body 50 and a table 51. In addition, the MRI apparatus 1 includes at least one RF coil 20 to be disposed close to the object. As described above, the RF coil 20 is also referred to as a local coil 20 or a surface coil 20.

The control cabinet 300 includes three gradient coil power supplies 31 (31x for an X-axis, 31y for a Y-axis, and 31z for a Z-axis), an RF receiver 32, an RF transmitter 33, and a sequence controller 34.

The static magnetic field magnet 10 of the gantry 2 is substantially in the form of a cylinder, and generates a static magnetic field inside a bore, which is a space formed inside the cylindrical structure and serves as an imaging region of the object (for example, a patient). The gradient coil assembly 11 is also substantially in the form of a cylinder and is fixed to the inside of the static magnetic field magnet 10. The gradient coil assembly 11 has a three-channel structure and includes an X-axis gradient coil, a Y-axis gradient coil, and a Z-axis gradient coil. Gradient magnetic fields Gx, Gy, and Gz are generated by respectively supplying the X-axis, Y-axis, and Z-axis gradient coils with electric currents from the gradient magnetic field power supplies 31x, 31y, and 31z, respectively.

The bed body 50 of the bed 500 can move the table 51 in the vertical direction and in the horizontal direction. The bed body 50 moves the table 51 with an object placed thereon to a predetermined height before imaging. Afterward, when the object is imaged, the bed body 50 moves the table 51 in the horizontal direction so as to move the object to the inside of the bore.

The WB body coil 12 is shaped substantially in the form of a cylinder so as to surround the object, and is fixed to the inside of the gradient coil assembly 11. The WB coil 12 applies RF pulses to be transmitted from the RF transmitter 33 to the object, and receives MR signals emitted from the object due to excitation of hydrogen nuclei.

The RF transmitter 33 transmits an RF pulse to the WB coil 12 on the basis of an instruction from the sequence controller 34. The RF receiver 32 detects an MR signal received by the WB coil 12 and/or the RF coil 20, and then transmits raw data obtained by digitizing the detected MR signal to the sequence controller 34.

The sequence controller 34 performs a scan of the object by driving the gradient coil power supplies 31, the RF transmitter 33, and the RF receiver 32 under the control of the console 400. When the sequence controller 34 performs a scan so as to receive raw data from the RF receiver 32, the sequence controller 34 transmits the raw data to the console 400.

The sequence controller 34 includes processing circuitry (not shown). This processing circuitry is configured as, for example, a processor for executing predetermined programs or configured as hardware such as a field programmable gate array (FPGA) and an application specific integrated circuit (ASIC).

The console 400 is configured as a computer that includes processing circuitry 40, a memory 41, a display 42, and an input interface 43.

The memory 41 is a recording medium including a read-only memory (ROM) and a random access memory (RAM) in addition to an external memory device such as a hard disk drive (HDD) and an optical disc device. The memory 41 stores various programs to be executed by a processor of the processing circuitry 40 as well as various data and information.

The display 42 is a display device such as a liquid crystal display panel, a plasma display panel, and an organic EL panel.

The input interface 43 includes various devices for an operator to input various data and information, and is configured of, for example, a mouse, a keyboard, a trackball, and/or a touch panel.

The processing circuitry 40 is, for example, a circuit provided with a central processing unit (CPU) and/or a special-purpose or general-purpose processor. The processor implements various functions described below by executing the programs stored in the memory 41. The processing circuitry 40 may be configured of hardware such as an FPGA and an ASIC. The various functions described below can also be implemented by such hardware. Additionally, the processing circuitry 40 can implement the various functions by combining hardware processing and software processing based on its processor and programs.

The MRI apparatus 1 includes at least one RF coil 20 in addition to the WB coil 12. The RF coil 20 receives MR signals emitted from the object at a position close to the object. The RF coil 20 includes a plurality of coil elements, for example. Depending on the anatomical imaging part of the object, there are various RF coils 20 such as for the head, for the chest, for the spine, for the lower limbs, and for the whole body. Of these various RF coils, FIG. 1 illustrates the RF coil 20 for imaging the chest.

The RF coil 20 of the MRI apparatus 1 according to the embodiments is configured as a wireless RF coil, which converts an MR signal received from the object into a digital signal and transmits it to a main body 600 wirelessly. Note that, in this specification, the term of "main body 600" herein is used for the configuration of the entire MRI apparatus 1 excluding the RF coil 20, the first communication circuitry, and second communication circuitry described below.

The RF coil 20 converts the received analog MR signal into a digital signal by using an A/D converter and wirelessly transmits the digitized MR signal to the main body 600, and thus, an AD clock for the A/D conversion is needed. Meanwhile, the main body 600 needs a processing clock that is synchronized with the AD clock used in the RF coil 20, in order to acquire the wirelessly received MR signals as digital data at an appropriate timing.

Accordingly, in the MRI apparatus 1 of the present embodiment, the main body 600 is configured to generate a system clock, then transmits the system clock wirelessly and constantly to the RF coil 20, while generating a processing clock therein from the system clock. The main body 600 and the RF coil 20 use this system clock in common, and thus can perform synchronized processing. In the present embodiments, the first communication circuitry 100 and the second communication circuitry 200 play a role of the wireless transmission of the system clock.

Figure 2A:
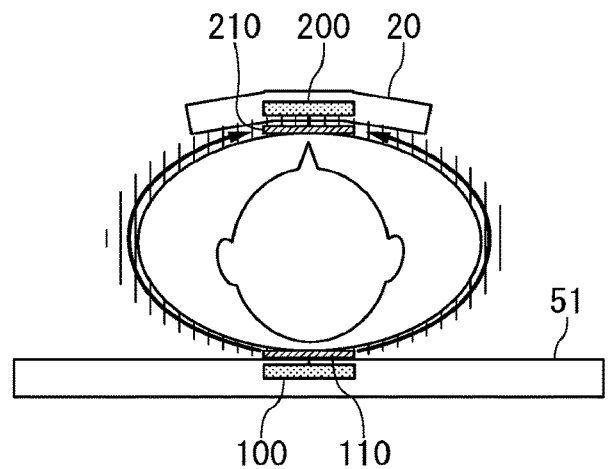
FIG. 2A and FIG. 2B are schematic diagrams for illustrating a disposition state of the first communication circuitry and the second communication circuitry with respect to the object and an electric-wave propagation state from the first communication circuitry to the second communication circuitry.
Figure 2B:
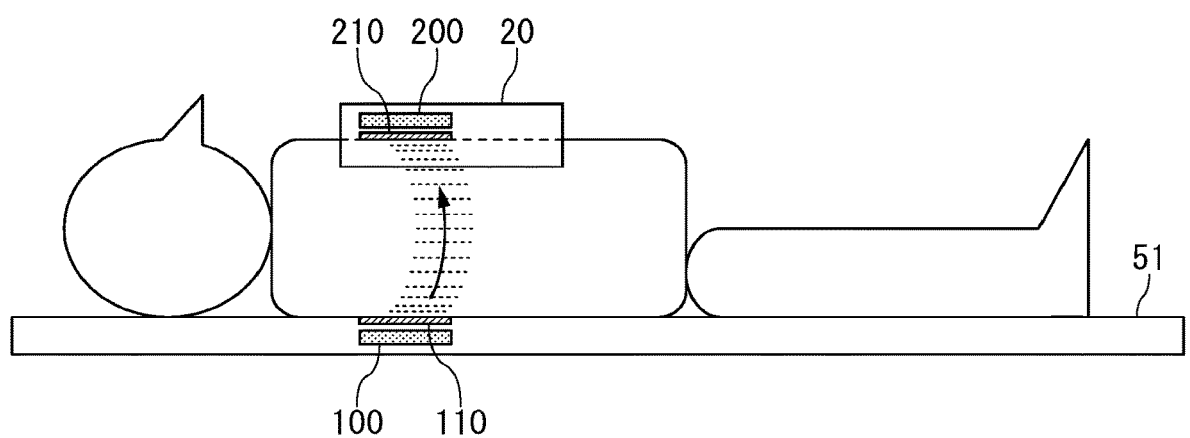

FIG. 2A and FIG. 2B are schematic diagrams for illustrating an arrangement of the first communication circuitry 100 and the second communication circuitry 200 with respect to the object. FIG. 2A and FIG. 2B further illustrates a wireless propagation from the first communication circuitry 100 to the second communication circuitry 200. It should be noted that in the MRI apparatus 1 of the present embodiment, wireless transmission of the system clock from the first communication circuitry 100 to the second communication circuitry 200 is performed on the basis of surface electric field communication by using electric field propagation along the body surface of the object. The surface electric field communication is also called quasi-electrostatic field communication.

Electromagnetic fields can be classified into a radiated electromagnetic field, an induced electromagnetic field, and a quasi-electrostatic field. The radiated electromagnetic field decays in inverse proportion to the distance, the induced electromagnetic field decays in inverse proportion to the square of the distance, and the quasi-electrostatic field decays in inverse proportion to the cube of the distance. Among these three, the radiated electromagnetic field (so-called radio wave) having the smallest attenuation with respect to distance is used for ordinary long-distance telecommunication.

The quasi-electrostatic field does not have the property of propagating through space like the radiated electromagnetic field, and is a voltage phenomenon distributed like an electrostatic charge near a substance such as a human body and a vehicle. While the temporal change of the electrostatic field can be regarded as zero, the quasi-electrostatic field temporally changes, and has a frequency component.

In the present embodiment, this quasi-electrostatic field is used for the communication between the first communication circuitry 100 and the second communication circuitry 200. Exciting an electric field due to capacitive coupling between the electrode 110 of the first communication circuitry 100 and the object (human body) and superimposing information of the system clock on the excited electric field enable the information of the system clock to be transmitted from the first communication circuitry 100 to the second communication circuitry 200 by using the surface of the human body as a transmission medium.

As shown in FIG. 2, the first communication circuitry 100 having the first electrode 110 may be disposed, for example, inside the table 51 of the bed 500, or at the top of the table 51. In particular, it is preferred that the first electrode 110 of the first communication circuitry 100 is disposed close to the object. For example, as shown in FIG. 2B, the first electrode 110 is disposed close to the back of the object. The first electrode 110 can be coated with an insulating coating. The first electrode 110 is not necessarily required to contact the skin of the object, and thus, may be disposed near the object via clothing. The first electrode 110 is, for example, a flat metal plate. Although the first electrode 110 is not limited to a specific dimension, the first electrode 110 may be a flat metal plate having a side or a diameter ranging from several centimeters to several tens of centimeters, for example.

The second communication circuitry 200 is disposed inside the RF coil 20. The second electrode 210 of the second communication circuitry 200 is disposed close to the object, similarly to the first electrode 110 of the first communication circuitry 100. For example, the second electrode is disposed close to the chest or abdomen of the object. The second electrode 210 may be also, for example, a flat metal plate having a side or a diameter ranging from several centimeters to several tens of centimeters, similarly to the first electrode 110.

Figure 3:
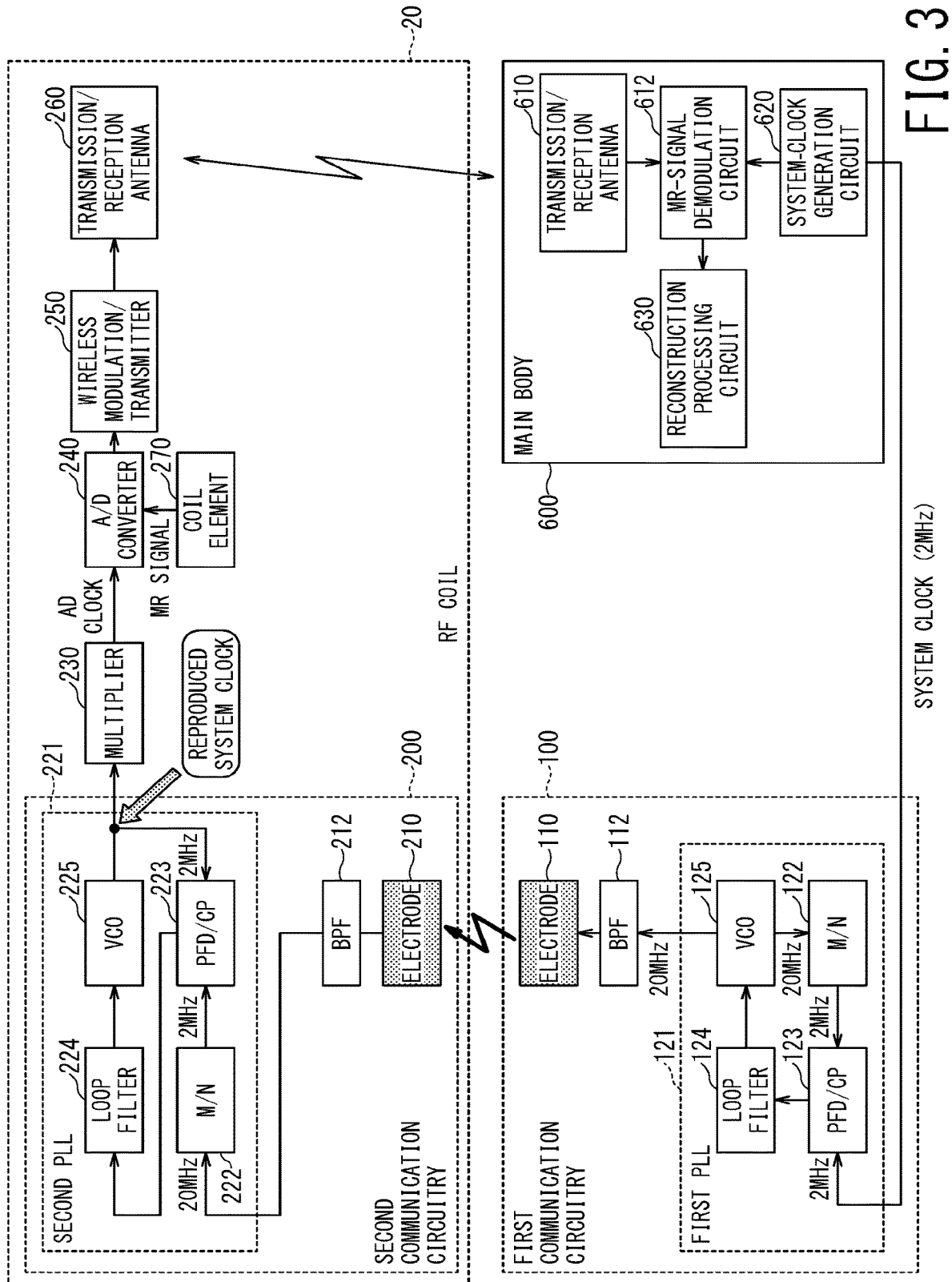
FIG. 3 is a block diagram illustrating a configuration of the first communication circuitry and the second communication circuitry according to the first embodiment.

FIG. 3 is a block diagram illustrating a configuration of the first communication circuitry 100 and the second communication circuitry 200 according to the first embodiment. FIG. 3 also shows the function of the main body 600 related to the communication and the communication information between the first communication circuitry 100 and the second communication circuitry 200.

The main body 600 includes a system-clock generation circuit 620, which generates the system clock. The system clock is used for the entire MRI apparatus 1, and the AD clock is generated from the system clock when the RF coil 20 performs A/D conversion on each MR signal. At the same time, a clock for acquiring the digital MR signal, which is wirelessly transmitted from the RF coil 20, to the main body 600 is also generated from the system clock.

As described above, the system clock is used for performing synchronized processing between the main body 600 and the RF coil 20. Therefore, it is necessary to send the system clock generated by the main body 600 to the RF coil 20.

Since the RF coil 20 of the present embodiment is configured as a wireless RF coil that transmits the MR signal to the main body 600 wirelessly, it is also necessary to wirelessly transmit the system clock generated by the main body 600 to the RF coil 20. In the MRI apparatus 1 of the present embodiment, the wireless transmission of the system clock is performed by using the above-described surface electric field communication along the body surface. The wireless transmission of the system clock is performed by using the first communication circuitry 100 and the second communication circuitry 200 shown in FIG. 3. In the following, while focusing on the wireless transmission of the system clock, the communication system of the present embodiment will be described.

The first communication circuitry 100 includes a first PLL (Phase Locked Loop) circuit 121, a band-pass filter (BPF) 112, and the first electrode 110, as shown in FIG. 3. The first PLL circuit 121 includes a phase comparator/charge pump (PFD/CP) 123, a loop filter 124, a VCO (voltage-controlled oscillator) 125, and a frequency divider (M/N) 122.

Although the clock frequency of the system clock generated by the main body 600 is not limited to a specific frequency, in the following, a description will be given of the case where the clock frequency of the system clock is 2 MHz, as one example.

The first PLL circuit 121 of the first communication circuitry 100 multiplies the frequency of the system clock, which is transmitted by wire from the main body 600, to generate a carrier signal for wirelessly transmitting the system clock from the first communication circuitry 100 to the second communication circuitry 200 by the surface electric field communication. Note that the carrier signal here is not a signal modulated by specific information or a specific waveform. Here, a clock signal obtained by simply multiplying the system clock is referred to as the carrier signal. In the following, the frequency of the carrier signal is referred to as the carrier frequency. Since the carrier signal is a signal obtained by multiplying the system clock by using the PLL circuit, the carrier signal and the system clock are signals synchronized with each other.

The band pass filter 112 removes unnecessary waves from the carrier signal, and the carrier signal after this filtering is wirelessly transmitted to the second electrode of the second communication circuitry 200 by the surface electric field communication with the use of the first electrode 110. The carrier frequency of the carrier signal is determined by the frequency of the system clock and the frequency division ratio of the frequency divider (M/N) 122. The clock frequency of the system clock is assumed to be 2 MHz as described above. Thus, when the frequency division ratio of the frequency divider (M/N) 122 is 1/10, the carrier frequency of the carrier signal will be 20 MHz.

Although the carrier frequency of the carrier signal is not limited to a specific range, from the viewpoint of suppressing reflection from any structure or substance distant from the object (i.e., imaging target), and reducing fading by suppressing the radiated electromagnetic field, a too high frequency is not desirable for the carrier frequency of the carrier signal. On the other hand, if the carrier frequency is set to a too low frequency, the carrier signal is likely to be affected by noise around the object. From such viewpoints, the carrier frequency of the carrier signal is set, for example, in the range of 1 MHz to several tens of MHz. In each embodiment, a description is given of the case where the carrier frequency of the carrier signal is 20 MHz. However, it should be noted that this frequency is only one example, and other frequencies may be used for the carrier frequency.

The carrier signal, which is wirelessly transmitted from the first electrode 110 of the first communication circuitry 100, is received by the second electrode 210 of the second communication circuitry 200. The second communication circuitry 200 includes a band-pass filter (BPF) 212 and a second PLL circuit 221 in addition to the second electrode 210. The second PLL circuit 221 includes a frequency divider (M/N) 222, a phase comparator/charge pump (PFD/CP) 223, a loop filter 224, and a VCO 225, similarly to the first PLL circuit 121.

The second PLL circuit 221 performs the opposite operation of the first PLL circuit 121. The first PLL circuit 121 generates the carrier signal by multiplying the system clock ten times, for example, from 2 MHz to 20 MHz. Conversely, the second PLL circuit 221 generates, or reproduces, the system clock by dividing the carrier signal by ten, for example, from 20 MHz to 2 MHz.

Since the divider (M/N) 122 of the first PLL circuit 121 and the divider (M/N) 222 of the second PLL circuit 221 have the same frequency dividing ratio (for example, 1/10), the frequency of the system clock inputted to the first communication circuitry 100 can be completely coincident with the frequency of the system clock outputted from the second communication circuitry 200, and thus, the respective phases of these two system clocks can be completely synchronized.

The second communication circuitry 200 is built in the RF coil 20 or is disposed close to the RF coil 20. In the RF coil 20, the MR signal received by the element coil 270 is converted into a digital signal by the A/D converter 240. The AD clock to be used at this time is obtained by multiplying the system clock outputted from the second communication circuitry 200 with the use of the multiplier 230 of the RF coil 20. Consequently, the AD clock used in the RF coil 20 becomes a clock signal that is synchronized with the system clock generated in the main body 600.

The MR signal converted into a digital signal is further converted into a signal suitable for wireless transmission by a wireless modulation/transmitter 250, and then is wirelessly transmitted from the transmission/reception antenna 260 to the transmission/reception antenna 610 of the main body 600. This wireless transmission may be achieved by a remote communication method using a radiated electromagnetic field, for example.

Subsequently, in the main body 600, each received MR signal is demodulated by the MR-signal demodulation circuit 612. Thereafter, the reconstruction processing circuit 630 performs reconstruction processing on the demodulated MR signals so as to generate an MR image.

In the MRI apparatus 1 of the first embodiment described above, the system clock generated by the main body 600 is wirelessly transmitted to the RF coil 20 by the surface electric field communication using electric field propagation along the body surface of the object. Thus, the system clock can be stably wirelessly transmitted from the main body 600 to the RF coil 20 without being affected by fading due to reflection from any structure or substance around the object.

First Modification of First Embodiment

Figure 4:
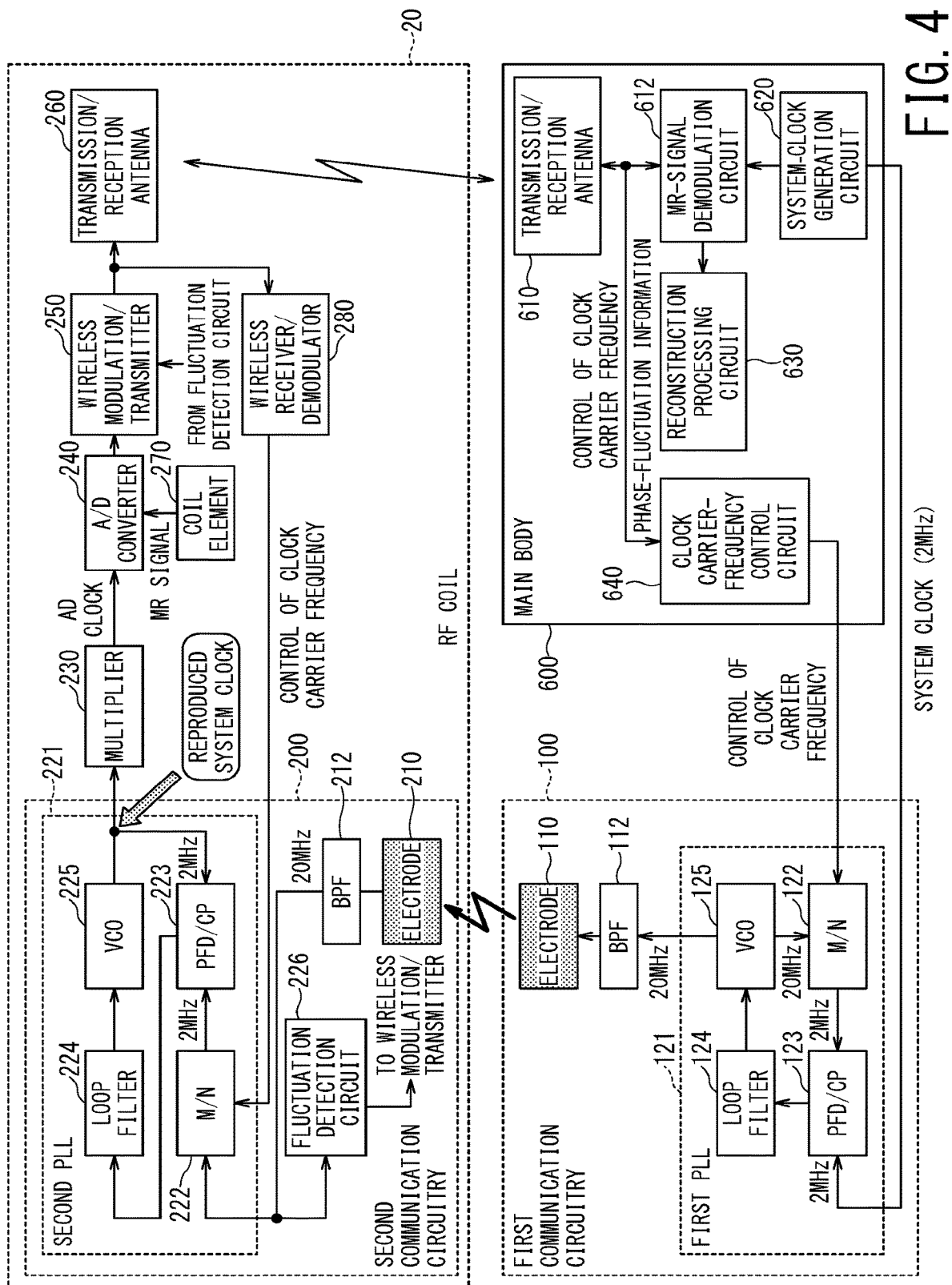
FIG. 4 is a block diagram illustrating a configuration of the first communication circuitry and the second communication circuitry according to the first modification of the first embodiment.

FIG. 4 is a block diagram illustrating a configuration of the first communication circuitry 100 and the second communication circuitry 200 according to the first modification of the first embodiment. As compared with the above-described first embodiment, the first modification of the first embodiment additionally has a function of detecting the phase fluctuation of the carrier signal and a function of setting the carrier frequency of the carrier signal so as to reduce the phase fluctuation.

The second communication circuitry 200 includes a fluctuation detection circuit 226 in order to implement the function of detecting the phase fluctuation of the carrier signal. Although the method of detecting fluctuation is not limited to a specific method, the fluctuation detection circuit 226 branches the carrier signal received by the second electrode 210 into the first path delayed by a delay element and the second path without delay, and then detects the phase difference between the respective output ends of the first path and the second path, for example. When no fluctuation is included in the phase of the carrier signal, this phase difference shows a constant value. By contrast, when fluctuation is included in the phase of the carrier signal, it is considered that this phase difference should fluctuate.

Information on the presence/absence and/or the degree of the phase fluctuation in the carrier signal detected by the fluctuation detection circuit 226 is sent to the main body 600 via the wireless modulation/transmitter 250. The main body 600 according to the first modification of the first embodiment includes a clock carrier-frequency control circuit 640. The clock carrier-frequency control circuit 640 adjusts the carrier frequency of the carrier signal such that the phase fluctuation is reduced, based on the presence/absence and/or the degree of the phase fluctuation in the carrier signal.

Specifically, the clock carrier-frequency control circuit 640 simultaneously changes the respective frequency dividing ratios of the frequency divider (M/N) 122 of the first communication circuitry 100 and the frequency divider (M/N) 222 of the second communication circuitry 200, by sending a control signal so as to search for the carrier frequency that reduces the phase fluctuation, and then sets the searched appropriate carrier frequency for the carrier signal. The control signal for changing the frequency dividing ratio of the frequency divider (M/N) 222 of the second communication circuitry 200 is wirelessly transmitted from the main body 600 to the RF coil 20, and then is sent to the frequency divider (M/N) 222 via the wireless receiver/demodulator 280 of the RF coil 20.

According to the first modification of the first embodiment, in addition to the effects of the first embodiment, the phase fluctuation of the carrier signal can be reduced, and consequently, the phase fluctuation of the system clock can also be reduced.

Second Modification of First Embodiment

Figure 5:
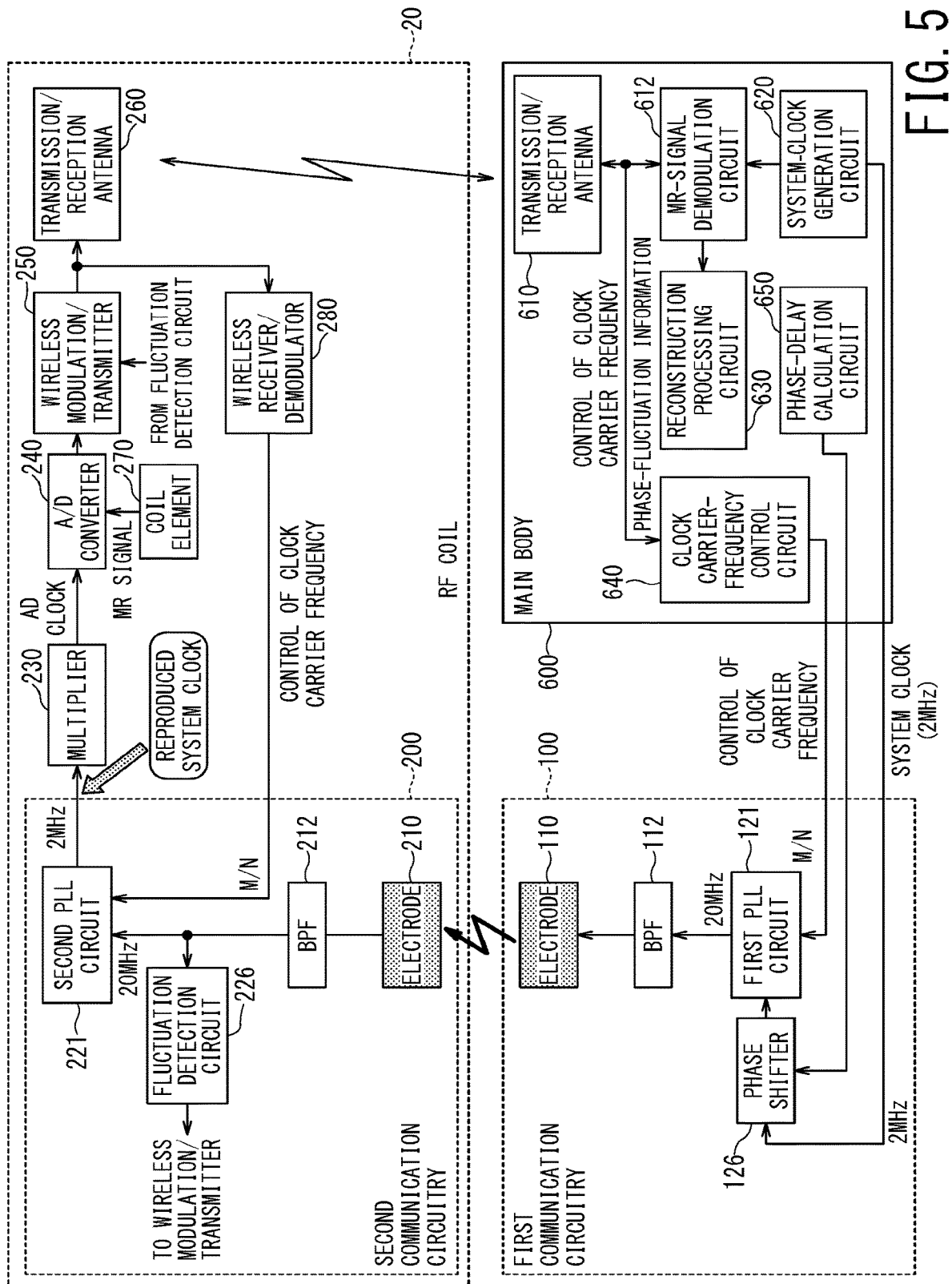
FIG. 5 is a block diagram illustrating a configuration of the first communication circuitry and the second communication circuitry according to the second modification of the first embodiment.

FIG. 5 is a block diagram illustrating a configuration of the first communication circuitry 100 and the second communication circuitry 200 according to the second modification of the first embodiment. In FIG. 5, the internal configuration of each of the first PLL circuit 121 and the second PLL circuit 221 is omitted in order to avoid complication.

In the second modification of the first embodiment, a function of shifting the phase of the system clock is added to the configuration of the first modification of the first embodiment. This additional function can be directly added to the first embodiment by removing the two functions added in the first modification.

In the second modification of the first embodiment, a phase-delay calculation circuit 650 is provided in the main body 600, and the phase-delay calculation circuit 650 calculates a desired phase shift amount of the system clock. In the surface electric field communication used in the present embodiment, the propagation path length varies depending on the size of the body of the object. Thus, the phase difference between the system clock of the transmission source of the first communication circuitry 100 and the system clock reproduced by the second communication circuitry 200 (i.e., phase difference caused by the delay amount) has different values depending on the size of the object, such as the thickness of the trunk (body) of the object.

Thus, in the second modification of the first embodiment, the phase delay calculation circuit 650 estimates the size of the object such as the thickness of trunk of the object by using image recognition technology, estimates the propagation path length from the first communication circuitry 100 to the second communication circuitry 200, and calculates the amount of phase correction.

The calculated phase correction amount is set in a phase shifter 126 provided in the first communication circuitry 100. The phase shifter 126 adjusts the phase of the system clock of the transmission source so as to correct the amount of the phase delay due to the propagation path length.

Third Modification of First Embodiment

Figure 6:
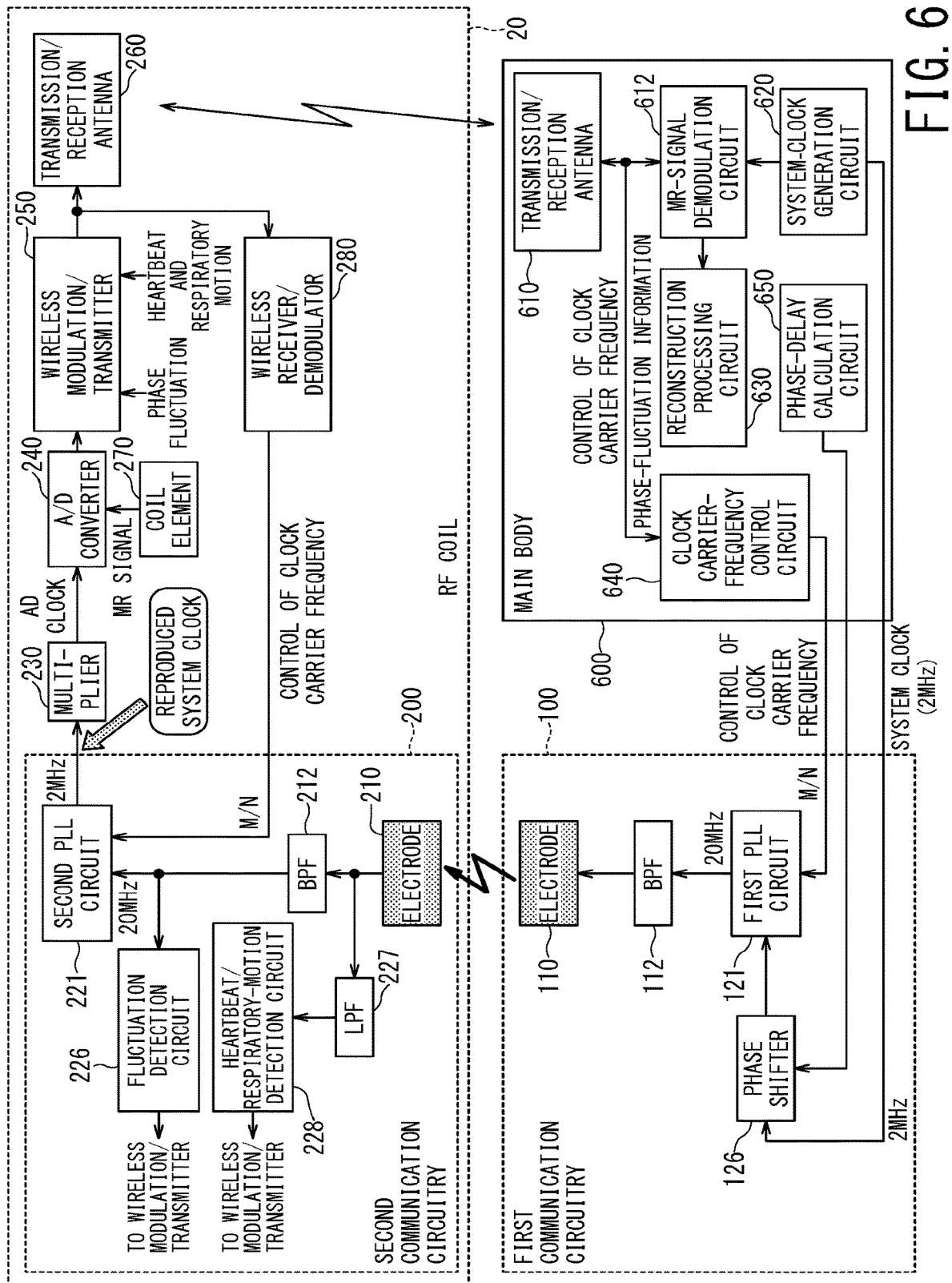
FIG. 6 is a block diagram illustrating a configuration of the first communication circuitry and the second communication circuitry according to the third modification of the first embodiment.

FIG. 6 is a block diagram illustrating a configuration of the first communication circuitry 100 and the second communication circuitry 200 according to the third modification of the first embodiment. As compared with the second modification of the first embodiment, the third modification of the first embodiment additionally includes a function of detecting a body motion such as heartbeat and a respiratory motion.

The carrier signal transmitted from the first communication circuitry 100 to the second communication circuitry 200 propagates along the body surface of the object from the first electrode 110 toward the second electrode 210 as shown in FIG. 2. Thus, when the body surface of the object fluctuates due to respiration and/or heartbeat, the carrier signal is subjected to amplitude modulation corresponding to the cycle of respiration and/or heartbeat and fluctuation range of respiration and/or heartbeat.

Thus, in the configuration of the third modification of the first embodiment, the second communication circuitry 200 is provided with a heartbeat/respiratory-motion detection circuit 228. The heartbeat/respiratory-motion detection circuit 228 functions as a biological monitoring circuit. The carrier signal received by the second electrode 210 passes through the band-pass filter 212 to be sent to the second PLL circuit 221 where the system clock is reproduced. Meanwhile, the carrier signal also passes through the low-pass filter 227 to be sent to the heartbeat/respiratory-motion detection circuit 228. The heartbeat/respiratory-motion detection circuit 228 detects the respiratory motion and/or heartbeat of the object on the basis of the amplitude fluctuation of the carrier signal and extracts information on the respiratory motion and/or heartbeat.

The heartbeat/respiratory-motion detection circuit 228 may detect biological information items such as a respiratory waveform, a heartbeat waveform, respiratory time-phase information based on the respiratory waveform, time-phase information of heartbeat based on the heartbeat waveform, a respiratory cycle, a respiratory rate, a heartbeat cycle, and/or a cardiac rate.

These biological information items detected by the heartbeat/respiratory-motion detection circuit 228 are transmitted to the wireless modulation/transmitter 250, and then wirelessly transmitted to the main body 600. The main body 600 can cause the display 42 to display the biological information items transmitted from the second communication circuitry 200. The main body 600 can also perform ECG-gated imaging and respiratory-gated imaging by using the heartbeat waveform and the respiratory waveform.

In the reconstruction processing performed by the reconstruction processing circuit 630, motion correction processing based on positional correction and/or phase correction may be performed by using the heartbeat waveform and the respiratory waveform transmitted from the second communication circuitry 200.

Second Embodiment

Figure 7:
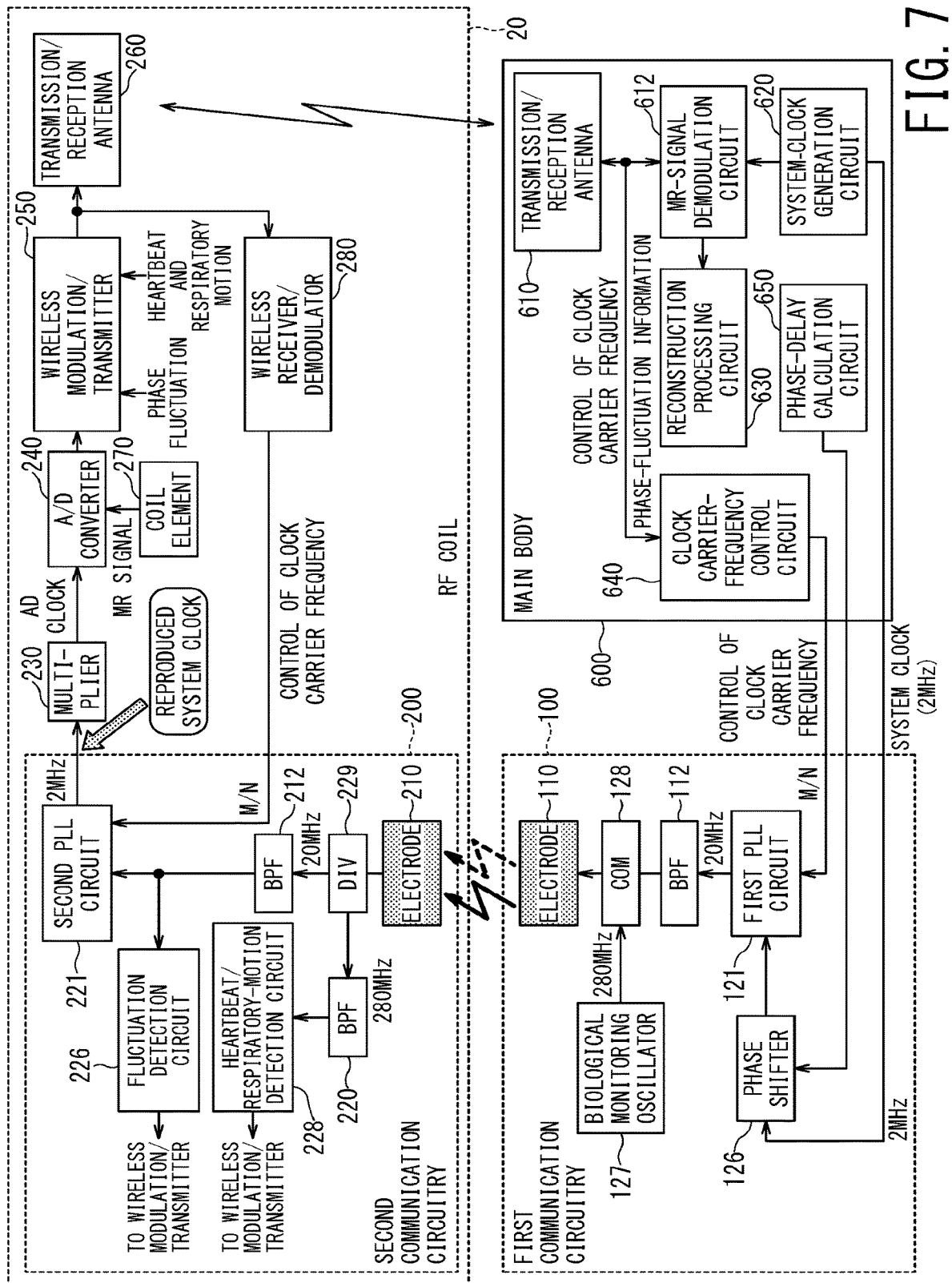
FIG. 7 is a block diagram illustrating a configuration of the first communication circuitry and the second communication circuitry according to the second embodiment.

FIG. 7 is a block diagram illustrating a configuration of the first communication circuitry 100 and the second communication circuitry 200 according to the second embodiment. In the second embodiment, the function of detecting a body motion such as heartbeat and a respiratory motion is added to the second modification of the first embodiment, similarly to the third modification of the first embodiment.

However, it should be noted that the configuration of the second embodiment detects a body motion, such as heartbeat and a respiratory motion, by a biological-information monitoring signal generated independently of the carrier signal of the system clock, while the configuration of the third modification of the first embodiment detects a body motion by using amplitude fluctuation of the carrier signal itself. The frequency of the biological-information monitoring signal of the second embodiments is selected so as to be different from the frequency of the carrier signal for transmitting the system clock.

The biological information monitoring signal is generated by a biological monitoring oscillator 127 provided in the first communication circuitry 100. The frequency of the biological-information monitoring signal is, for example, 280 MHz, and a frequency higher than the carrier frequency 20 MHz of the carrier signal is selected as the frequency of the biological-information monitoring signal.

The biological-information monitoring signal and the carrier signal for clock transmission are combined by a combiner 128 and then wirelessly transmitted from the first electrode 110 to the second electrode 210 of the second communication circuitry 200. In the second communication circuitry 200, the combined signal of the biological-information monitoring signal and the carrier signal for clock transmission is divided into two by a divider 229. One of the divided signals is transmitted to the second PLL circuit 221 through the band-pass filter 212 having the center frequency of 20 MHz, and another of divided signals is transmitted to the heartbeat/respiratory-motion detection circuit 228 through the band-pass filter 220 having the center frequency of 280 MHZ.

The heartbeat/respiratory-motion detection circuit 228 detects a body motion such as heartbeat and a respiratory motion by detecting change in magnitude of the transmitted signal of the biological-information monitoring signal from the first electrode 110 to the second electrode 210.

The block diagram of the second embodiment shown in FIG. 7 includes: the function (A), which is achieved by the components such as the fluctuation detection circuit 226 and the clock carrier-frequency control circuit 640, of detecting the phase fluctuation of the system clock carrier signal and adjusting the carrier frequency to reduce the phase fluctuation; and the function (B), which is achieved by the components such as the phase shifter 126 and the phase-delay calculation circuit 650, of correcting the phase delay attributable to the propagation path length of the system clock. However, the entire communication system may be configured such that one or both of the function (A) of adjusting the carrier frequency and the function (B) of correcting the phase delay may be omitted from the configuration of the second embodiment.

Figure 8A:
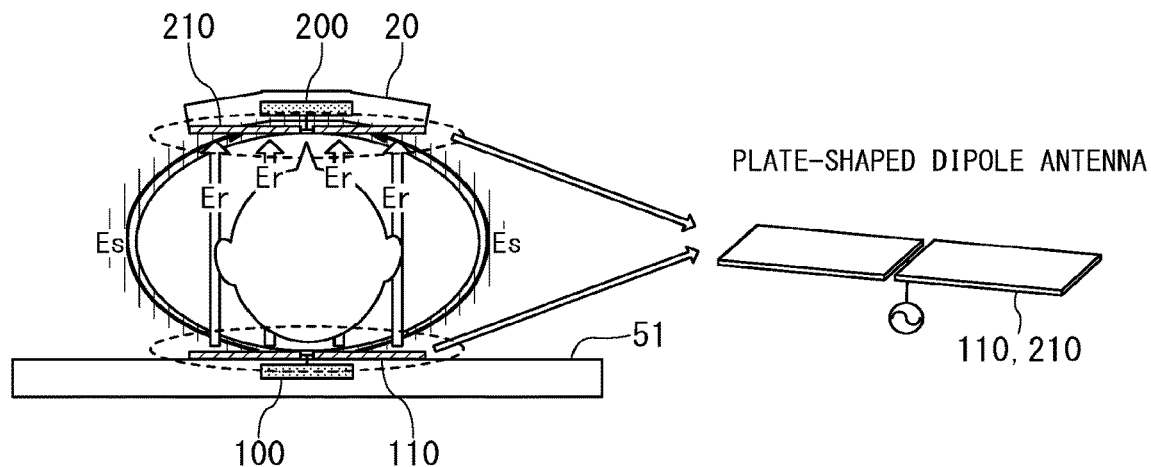
FIG. 8A and FIG. 8B are schematic diagrams illustrating a disposition state of the first and second electrodes to be used in the second embodiment and a propagation state of an electric field between the first and second electrodes.
Figure 8B:
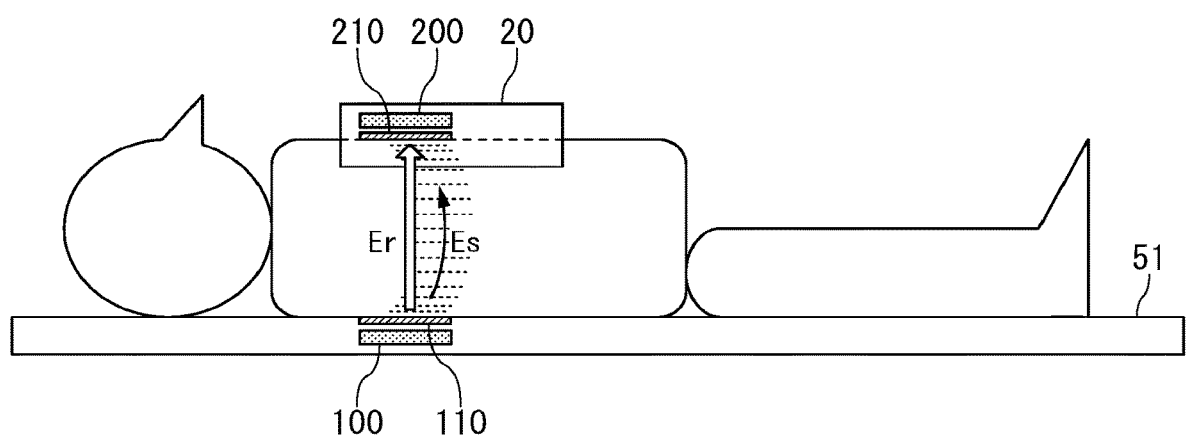

FIG. 8A and FIG. 8B are schematic diagrams illustrating how the first electrode 110 in the first communication circuitry 100 and the second electrode 210 in the second communication circuitry 200 according to the second embodiment are arranged, and how an electric field propagates between the first electrode 110 and the second electrode 200. As shown in the right part of FIG. 8A, the first electrode 110 and the second electrode 210 are configured as a plate-shaped dipole antenna.

Note that the element of the dipole antenna is formed in a plate shape, instead of a usual rod shape. This configuration makes it easy to excite an electric field due to capacitive coupling with the object (human body) and can realize an antenna suitable for the surface electric field communication, in which an electric wave propagates on the body surface in a near field (quasi-electrostatic field) Es using a relatively low frequency. Meanwhile, a half-wave dipole antenna is formed by feeding power to the center of two plate-shaped elements, which achieves communication in the far field (radiation field) Er using a frequency (for example, 280 MHz) higher than the carrier frequency at the same time.

It is known that the near field (quasi-electrostatic field) Es readily propagates in the longitudinal direction of the electrode when the plate-shaped electrode is rectangular. For this reason, it is preferred to dispose the plate-shaped dipole antenna such that the longitudinal direction thereof is orthogonal to the head-foot direction of the object (i.e., parallel to the right-left direction of the object). This is because the direction in which the carrier signal readily propagates coincides with the direction in which the propagation path length becomes shorter.

First Modification of Second Embodiment

In the second embodiment, the heartbeat/respiratory-motion detection circuit 228 provided in the second communication circuitry 200 detects the change in magnitude of the transmitted signal of the biological-information monitoring signal from the first electrode 110 to the second electrode 210 so that a body motion such as heartbeat and a respiratory motion is detected.

Instead of detecting a body motion by the transmitted signal, the entire system may be configured such that a directional coupler (not shown) is provided between the combiner 128 and the first electrode 110 and the first communication circuitry 100 includes a heartbeat/respiratory-motion detection circuit (not shown) configured to detect the fluctuation of the reflected signal from the first electrode 110. In this case, the heartbeat/respiratory-motion detection circuit of the first communication circuitry 100 detects change in coupling amount of the near-field coupling between the object and the first electrode 110. That is, the coupling amount of the near-field coupling between the object and the first electrode 110 fluctuates due to the body motion of the object such as heartbeat and a respiratory motion, and thus, the matching situation of the first electrode 110 with respect to the biological-information monitoring signal fluctuates, resulting in that the reflected signal of the biological-information monitoring signal from the first electrode 110 fluctuates. Accordingly, in the first modification of the second embodiment, a body motion such as heartbeat and a respiratory motion is detected by detecting change in the reflected signal.

Second Modification of Second Embodiment

The second modification of the second embodiment is a configuration in which the second embodiment and the first modification of the second embodiment are combined as to detection of a body motion such as heartbeat and a respiratory motion. In other words, in the configuration of the second modification of the second embodiment, the second communication circuitry 200 is provided with the heartbeat/respiratory-motion detection circuit 228 and the first communication circuitry 100 is also provided with the heartbeat/respiratory-motion detection circuit.

The heartbeat/respiratory-motion detection circuit 228 of the second communication circuitry 200 detects the fluctuation of magnitude of the transmitted signal of the biological-information monitoring signal from the first electrode 110 to the second electrode 210. Meanwhile, the heartbeat/respiratory-motion detection circuit of the first communication circuitry 100 detects the fluctuation of magnitude of the reflected signal of the biological-information monitoring signal from the first electrode 110. Further, diversity processing is performed on the fluctuation of the transmitted signal and the fluctuation of the reflected signal to detect a body motion such as heartbeat and/or a respiratory motion. For example, the fluctuation width of the transmitted signal is compared with the fluctuation width of the reflected signal, and the body motion such as heartbeat and/or a respiratory motion is detected from the signal having the larger fluctuation width.

Third Modification of Second Embodiment

Figure 9A:
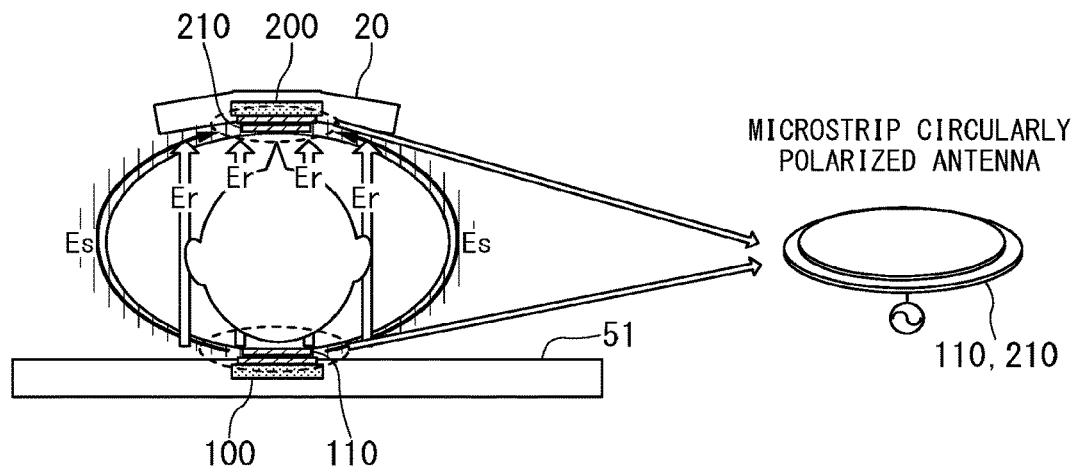
FIG. 9A and FIG. 9B are schematic diagrams illustrating the first and second electrodes to be used in the third modification of the second embodiment.
Figure 9B:
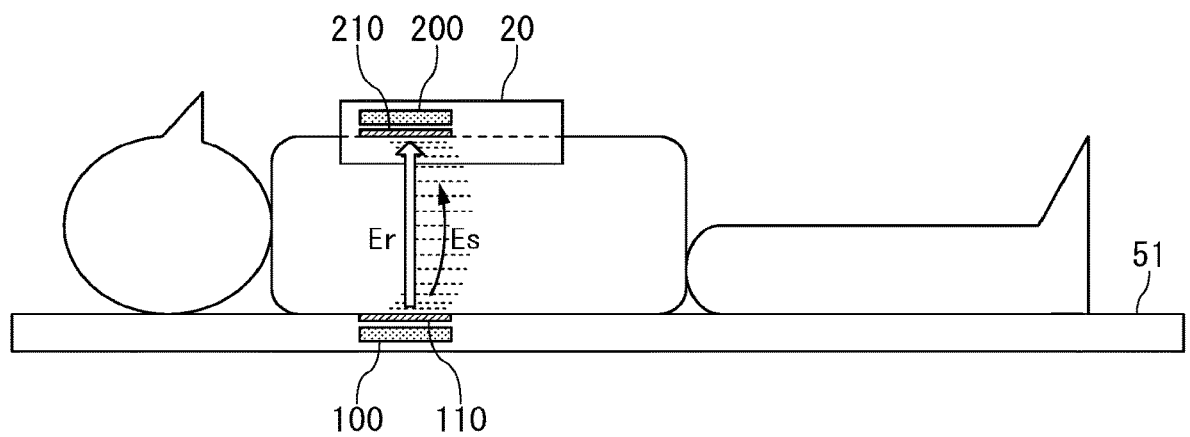

FIG. 9A and FIG. 9B are schematic diagrams illustrating the first electrode 110 and the second electrode 210 used in the first communication circuitry 100 and the second communication circuitry 200 according to the third modification of the second embodiment. In the second embodiment, a plate-shaped dipole antenna is used as the first electrode 110 and the second electrode 210 (FIG. 8). In the third modification of the second embodiment, a microstrip circularly polarized antenna is used instead of the plate-shaped dipole antenna.

The use of the microstrip circularly polarized antenna for both the first electrode 110 and the second electrode 210 makes the quasi-electrostatic field Es approximately omnidirectional (or nondirectional) for the surface electric field communication. Thus, even if the first electrode 110 and the second electrode 210 are displaced with respect to the body surface or are misaligned (or misoriented) with each other, both electrodes 110 and 210 are less likely to be affected by the displacement or misalignment (misorientation).

In addition, the use of the circularly polarized waves makes it less likely to be affected by primary reflected signals from around the object. This is because the rotational direction of the circularly polarized wave in the case of the primary reflection signal is reversed.

Instead of the microstrip circularly polarized antenna, a cross dipole antenna in which two plate-shaped dipole antennas are arranged so as to be orthogonal to each other can be used. Circular polarization can be realized by the cross dipole antenna as well. The cross dipole antenna also has wide-angle directivity close to the microstrip circularly polarized antenna as compared with the dipole antenna, and can be made less susceptible to the displacement and misorientation of the first electrode 110 and the second electrode 210.

Fourth Modification of Second Embodiment

Figure 10:
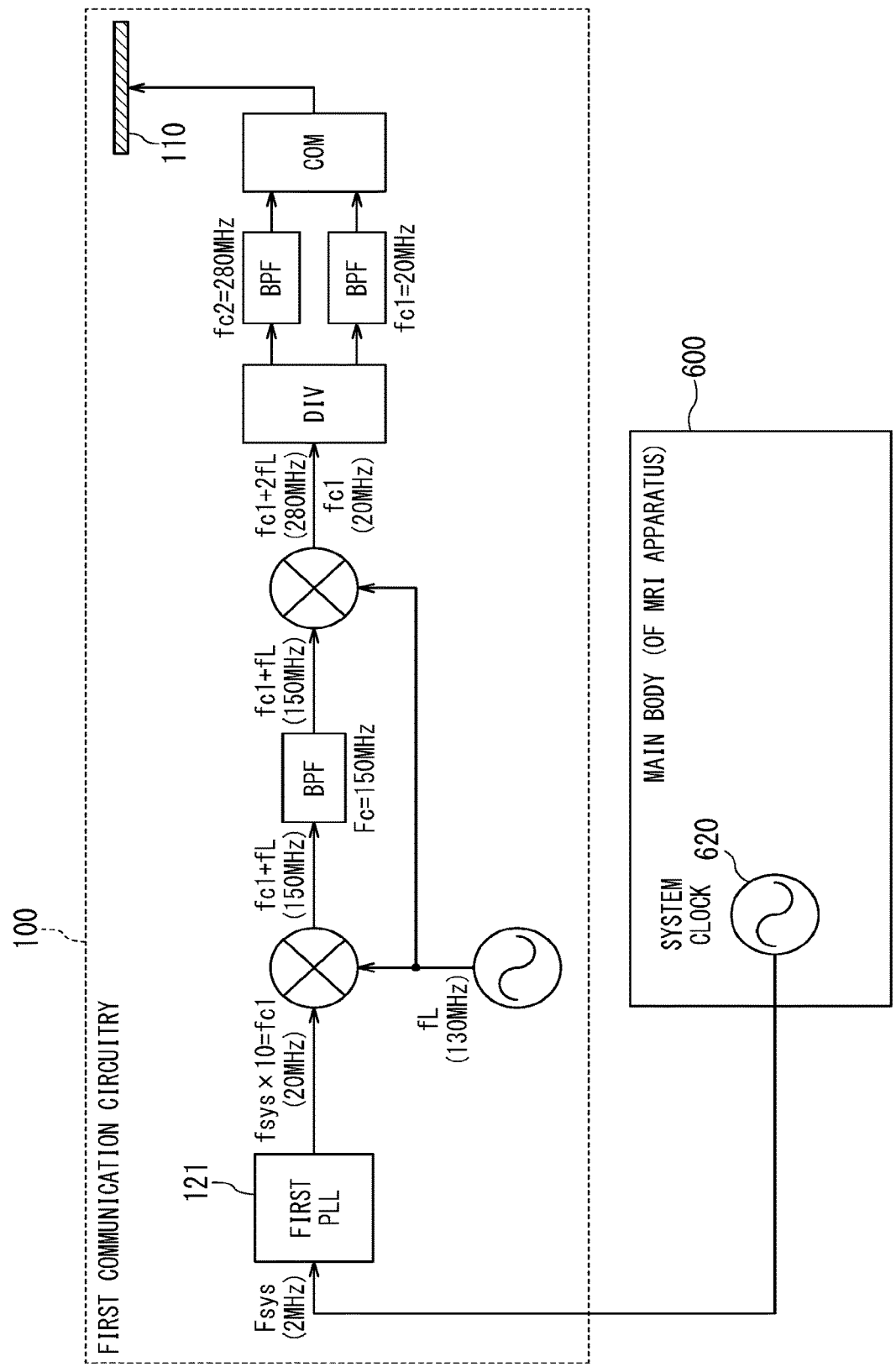
FIG. 10 is a block diagram illustrating a configuration of the first communication circuitry according to the fourth modification of the second embodiment.

FIG. 10 is a block diagram illustrating a configuration of the first communication circuitry 100 according to the fourth modification of the second embodiment. FIG. 10 focuses particularly on the components related to generation of the carrier signal of the system clock (center frequency fc1, for example, 20 MHz) and the biological-information monitoring signal (center frequency fc2, for example, 280 MHz).

The system clock (clock frequency fsys, for example, 2 MHz) generated by the system-clock generation circuit 620 of the main body 600 is converted into a frequency fc1 (=20 MHz) of ten times by the first PLL circuit 121 of the first communication circuitry 100.

The first communication circuitry 100 has a local oscillator with a local frequency fL (=130 MHz). The leftmost mixer in FIG. 10 mixes the output signal of the first PLL circuit 121 and the output signal of the local oscillator, and generates an intermediate signal of an intermediate frequency (fc1+fL=150 MHz, fc1−fL=110 MHz). As to these two frequencies (150 MHz and 110 MHz), the intermediate signal having the frequency of 150 MHz is selected by the band-pass filter having the center frequency Fc (=150 MHz), and further mixed with the output signal of the local oscillator by the second leftmost mixer. The output of this mixer includes: the sum frequency (fc1+2fL=280 MHz) of the intermediate frequency (fc1+fL=150 MHz) and the local frequency fL (=130 MHz); and the difference frequency (fc1=20 MHz) between the intermediate frequency (fc1+fL=150 MHz) and the local frequency fL. The divider and two band-pass filters, which are connected to the output stage of the mixer, extract the signal corresponding to the sum frequency (=280 MHz) as the biological-information monitoring signal and also extract the signal corresponding to the difference frequency (=20 MHz) as the carrier signal of the system clock. Subsequently, these two signals are combined by a combiner and transmitted from the first electrode 110.

Fifth Modification of Second Embodiment

Figure 11:
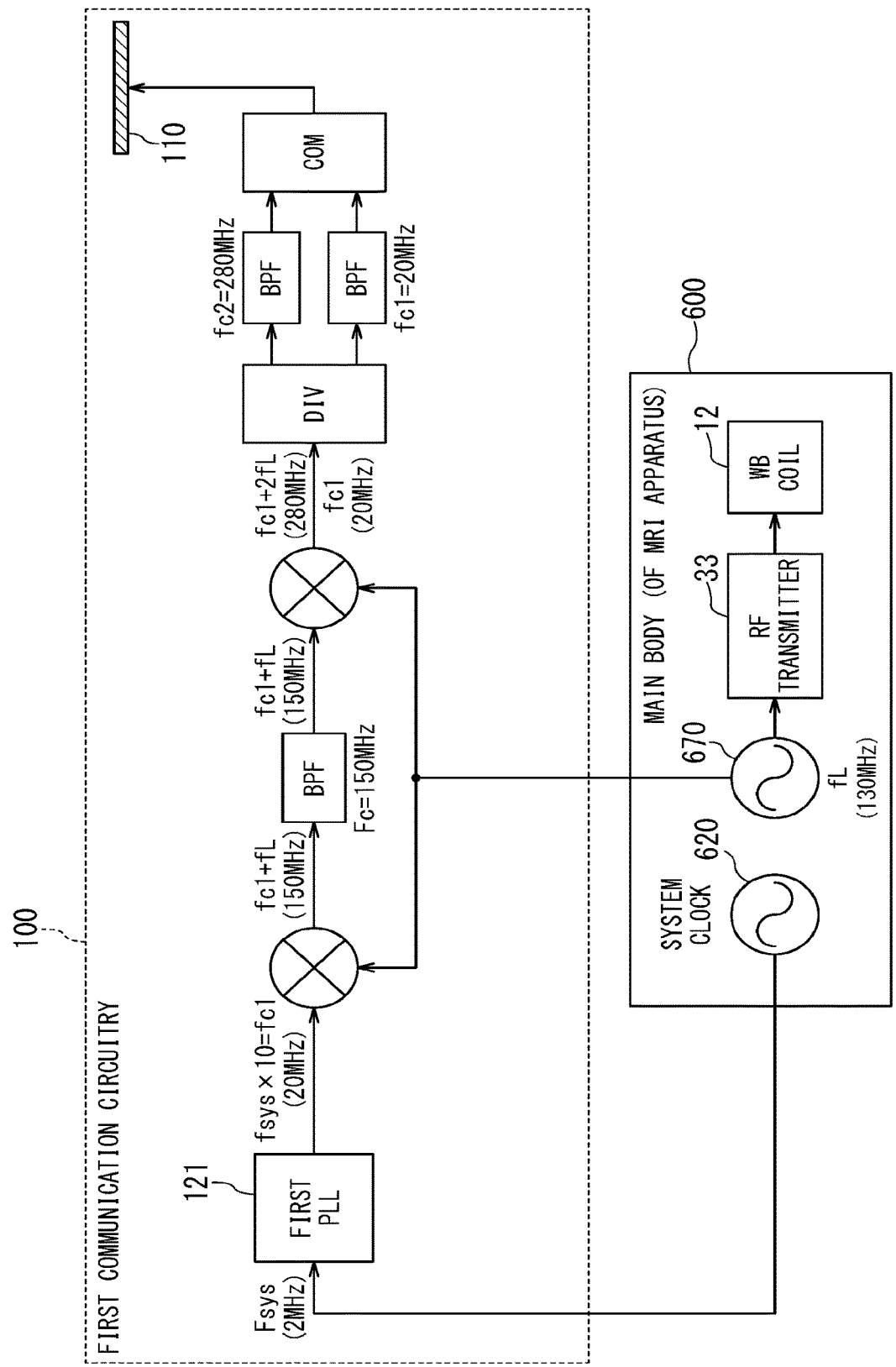
FIG. 11 is a block diagram illustrating a configuration of the first communication circuitry according to the fifth modification of the second embodiment.

FIG. 11 is a block diagram illustrating a configuration of the first communication circuitry 100 according to the fifth modification of the second embodiment. The configuration of the fourth modification of the second embodiment has the local oscillator of the local frequency fL (=130 MHz) in the first communication circuitry 100. In the fifth modification of the second embodiment, without having a local oscillator in the first communication circuitry 100, the output signal of the oscillator 670 provided in the main body 600 is used as a local signal of each mixer of the first communication circuitry 100.

The output signal of the oscillator 670 of the main body 600 generates an RF pulse for exciting hydrogen nuclei of the object to emit an MR signal, and is outputted from the RF transmitter 33 via the WB coil 12 to the object. When the static magnetic field of the MRI apparatus 1 is 3 Tesla, the frequency of the output signal of the oscillator 670 is the Larmor frequency of 130 MHz. Thus, in the fifth modification of the second embodiment, the Larmor frequency may be used as the local frequency fL (=130 MHz) in the first communication circuitry 100.

According to the fifth modification of the second embodiment, the local oscillator in the first communication circuitry 100 is not required. Further, the frequency of the biological-information monitoring signal does not match the harmonics of the Larmor frequency, and thus, is not affected by harmonics of the RF pulse generated by the main body 600.

According to the MRI apparatus 1 of each embodiment described above, the system clock can be stably transmitted from the main body of the MRI apparatus to the wireless RF coil without being affected by fading, and biological information such as heartbeat and/or respiration of the object can be readily obtained without imposing a burden on the object.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A Magnetic Resonance Imaging (MRI) apparatus, comprising:
    an RF coil configured to perform A/D conversion on a magnetic resonance (MR) signal received from an object and wirelessly transmit the MR signal;
    a main body configured to wirelessly receive the MR signal and generate a system clock;
    first communication circuitry configured to transmit the system clock by surface electric field communication using electric field wireless propagation along a body surface of the object; and
    second communication circuitry provided in the RF coil and configured to receive the system clock transmitted by the surface electric field communication,
    wherein the RF coil is configured to operate based on the received system clock, using the electric field wireless propagation from the first communication circuitry.

2. The MRI apparatus according to claim 1, wherein:
    the first communication circuitry includes a first electrode disposed on one side of the object; and
    the second communication circuitry includes a second electrode that is provided in the RF coil and is disposed on another side of the object.

3. The MRI apparatus according to claim 1, wherein:
    the second communication circuitry is further configured to detect a phase fluctuation of the received system clock and transmit information on detected phase fluctuation to the main body; and
    the main body is further configured to set a carrier frequency for transmitting the system clock from the first communication circuitry to the second communication circuitry in such a manner that the phase fluctuation is reduced.

4. The IRI apparatus according to claim 1, wherein the main body is further configured to estimate a propagation path length from the first communication circuitry to the second communication circuitry and correct a phase delay of the system clock corresponding to the propagation path length.

5. The MRI apparatus according to claim 1, wherein the second communication circuitry further includes a biological monitoring circuit configured to detect biological information from a change in signal intensity of the received system clock, the biological information including at least one of heartbeat and a respiratory motion of the object.

6. The MRI apparatus according to claim 1, wherein:
the first communication circuitry is further configured to
combine a first high-frequency signal for transmitting the system clock by the surface electric field communication and a second high-frequency signal for detecting biological information including at least one of a heartbeat and a respiratory motion of the object by radiated electromagnetic field communication, and
transmit a combined signal of the first high-frequency signal and the second high-frequency signal to the second communication circuitry; and
the second communication circuitry is further configured to
separate the first high-frequency signal and the second high-frequency signal from the combined signal,
reproduce the system clock from the separated first high-frequency signal, and
detect the biological information from a change in signal intensity of the separated second high-frequency signal.

7. The MRI apparatus according to claim 6, wherein:
the first communication circuitry is provided with a first plate-shaped dipole antenna disposed on one side of the object;
the second communication circuitry is provided with a second plate-shaped dipole antenna that is provided inside the RF coil and is disposed on another side of the object; and
the first plate-shaped dipole antenna and the second plate-shaped dipole antenna are configured to perform communication corresponding to both of the surface electric field communication and the radiated electromagnetic field communication.

8. The MRI apparatus according to claim 7, wherein each of the first plate-shaped dipole antenna and the second plate-shaped dipole antenna is disposed in such a manner that a longitudinal direction of each of the first plate-shaped dipole antenna and the second plate-shaped dipole antenna is orthogonal to a head-foot direction of the object.

9. The MM apparatus according to claim 6, wherein:
the first communication circuitry is provided with a first circularly polarized antenna disposed on one side of the object;
the second communication circuitry is provided with a second circularly polarized antenna that is provided inside the RF coil and is disposed on another side of the object; and
the first circularly polarized antenna and the second circularly polarized antenna are configured to perform communication corresponding to both of the surface electric field communication and the radiated electromagnetic field communication.

10. The MRI apparatus according to claim 6, wherein:
the second communication circuitry is further configured to detect a phase fluctuation of the received system clock and transmit information on the detected phase fluctuation to the main body;
the main body is further configured to set a carrier frequency for transmitting the system clock from the first communication circuitry to the second communication circuitry in such a manner that the phase fluctuation is reduced.

11. The MRI apparatus according to claim 6, wherein a frequency of the second high-frequency signal is set to a higher frequency than a frequency of the first high-frequency signal.

12. The MRI apparatus according to claim 11, wherein the second high-frequency signal is generated from a signal source that is a generation source of a high-frequency transmission pulse for obtaining the MR signal the signal source having a Larmor frequency of the object.

13. The MRI apparatus according to claim 5, wherein:
the second communication circuitry is further configured to transmit the biological information to the main body; and
the main body is further configured to use the biological information for correcting a motion of the object in reconstruction processing of the MR signal.

14. A communication method of a Magnetic Resonance Imaging (MRI) apparatus that includes an RF coil configured to perform A/D conversion on a magnetic resonance (MR) signal received from an object and wirelessly transmit the MR signal, and a main body configured to wirelessly receive the MR signal and generate a system clock, the communication method comprising:
transmitting the system clock from first communication circuitry disposed on one side of the object by surface electric field communication using electric field wireless propagation along a body surface of the object;
receiving, by second communication circuitry provided in the RF coil, the system clock transmitted by the surface electric field communication using the electric field wireless propagation from the first communication circuitry; and
operating the RF coil based on the received system clock.

* * * * *